United States Patent
Watson et al.

[11] Patent Number: 5,831,742
[45] Date of Patent: Nov. 3, 1998

[54] PORTABLE ELECTROMETRIC APPARATUS FOR ROADSIDE ANALYSIS OF AUTOMOTIVE EXHAUST EMISSION

[75] Inventors: Joseph Watson; Reza Tamadoni, both of Swansea; Barbara L. Jones, Norfolk; Kenneth W. Peter; Thomas F. Wylie, both of Cambs, all of United Kingdom

[73] Assignee: Sun Electric U.K. Limited, King's Lynn, England

[21] Appl. No.: 659,328

[22] Filed: Jun. 6, 1996

[30] Foreign Application Priority Data

Jun. 16, 1995 [GB] United Kingdom ............... 9512278

[51] Int. Cl.$^6$ ............................................. G01J 3/08
[52] U.S. Cl. ........................... 356/434; 356/325; 356/437
[58] Field of Search .................... 356/445, 325, 356/432, 437, 434; 385/22

[56] References Cited

U.S. PATENT DOCUMENTS

| | | | |
|---|---|---|---|
| 3,667,293 | 6/1972 | Moore | 73/179 |
| 3,730,627 | 5/1973 | Kent | 356/434 |
| 4,023,905 | 5/1977 | Chance | 356/325 |
| 4,212,513 | 7/1980 | Gravel | 385/22 |
| 4,303,302 | 12/1981 | Ramsey et al. | 385/22 X |
| 4,467,236 | 8/1984 | Kolm et al. | 310/321 |

(List continued on next page.)

FOREIGN PATENT DOCUMENTS

| | | |
|---|---|---|
| 79-00464 | 7/1979 | Japan. |
| 2101299 | 1/1983 | United Kingdom. |
| 9105252 | 4/1991 | WIPO. |

OTHER PUBLICATIONS

J.D. Ingle & S.R. Crouch, "Spectrochemical Analysis," pp. 44–47, (Prentice–Hall Int.Ed., 1988), Chap. 3, sections 3 and 4; pp. 47–60, Chap. 4, section 6; pp. 128–132, Chap. 4, section 6.

C.N. Banwell, "Fundamentals of Molecular Spectroscopy," Ed. 3 (McGraw–Hill, 1983), Chap. 3, section 8, pp. 111–123.

J. Jackson, "Infra–red Gas Analyzers Using Solid State Devices", Proc 1st Eur. Electro–optics Markets and Technology Conf. (IPC Sc. & Tech. Press, 1972, pp. 17–22.).

J.D. Ingle & S.R. Crouch, "Spectrochemical Analysis", (Prentice–Hall Int. Ed., 1988), Chap. 3, sections 3 & 4, chap. 4, section 6.

C.N. Branwell, "Fundamentals of Molecular Spectroscopy", Ed. 4 (McGraw–Hill, 1983), Chap. 3 section 8.

H.N. McMurray, "Novel thin optical film sensors for the detection of carbon dioxide", J Mat. Chem., 2(4), 401–406, 1992.

A. Mills, Quing Chang & H. N. Murray, "Equilibrium studies on colorimetric plastic film sensors for carbon dioxide", Anal. Chem. 64, 1383–1389, 1992.

J. Watson, R. Tamadoni–Jahromi, N. McMurray & G.S.V. Coles, "A Gas Monitoring Instrument Comprising Fibre Optic, Piezo–electric and Gas–Sensitive Polymer Devices", Transducers '95, Stockholm, Jun. 1995.

Primary Examiner—Vincent P. McGraw
Attorney, Agent, or Firm—Emrich & Dithmar

[57] ABSTRACT

A method and apparatus for instantaneously measuring the level of carbon dioxide (and other gases) in automotive combustion exhaust analysis is provided in the form of a portable battery driven roadside diagnostic instrument in which the $CO_2$ level is measured by a calorimetric technique utilizing light as the energy source and a piezoelectric bimorph to vibrate a single fiber-optic element to multiplex between two fiber-optic receptors delivering the light to a measurement cell and a reference cell. The measurement cell comprises a salt of an acid-base indicator dye which provides proportional color change on contact with $CO_2$. The dye is supported on a polymetric film in the cell.

4 Claims, 4 Drawing Sheets

U.S. PATENT DOCUMENTS

| | | | |
|---|---|---|---|
| 4,661,320 | 4/1987 | Ito et al. | 356/432 X |
| 4,718,765 | 1/1988 | Fortunato et al. | 356/346 |
| 4,820,045 | 4/1989 | Boisde et al. | 356/319 |
| 4,893,934 | 1/1990 | Hansen | 356/434 |
| 4,914,719 | 4/1990 | Conlon et al. | 250/339 |
| 4,928,687 | 5/1990 | Lampotang et al. | 128/207.14 |
| 4,994,117 | 2/1991 | Fehder | 436/133 |
| 5,060,505 | 10/1991 | Tury et al. | 73/1 G |
| 5,071,526 | 12/1991 | Pletcher et al. | 204/153.1 |
| 5,114,859 | 5/1992 | Kagenow | 436/50 |
| 5,131,746 | 7/1992 | O'Rourke et al. | 356/325 X |
| 5,184,017 | 2/1993 | Tury et al. | 250/343 |
| 5,206,701 | 4/1993 | Taylor et al. | 356/325 |
| 5,216,315 | 6/1993 | Terada et al. | 310/329 |
| 5,223,715 | 6/1993 | Taylor | 356/319 |
| 5,252,828 | 10/1993 | Kert et al. | 250/339 |
| 5,343,043 | 8/1994 | Johnson | 250/338.5 |
| 5,375,592 | 12/1994 | Kirk et al. | 128/207.14 |
| 5,472,668 | 12/1995 | Mills et al. | 422/56 |

PORTABLE ELECTROMETRIC APPARATUS FOR ROADSIDE ANALYSIS OF AUTOMOTIVE EXHAUST EMISSION

BACKGROUND OF THE INVENTION

1. Field of the Invention

This invention relates to a method and apparatus for gas monitoring. The invention is particularly applicable to the monitoring of carbon dioxide in automotive combustion exhaust analysis, but is applicable to the monitoring and analysis of other gases and in other applications. A particular example of the application of the invention is to the provision of a portable battery-driven roadside automotive diagnostic instrument. Broadly, the invention provides a method and apparatus for electrometric analysis of a sample of a material, such as a gas to be analyzed. The term "electrometric" is used to designate a technique including photometric analysis, but not limited to electromagnetic radiation of visible wavelength, and thus covering techniques analogous to photometric analysis (as described in the specific embodiment) but in which electromagnetic radiation of longer or shorter wavelength is employed.

2. Description of the Prior Art

Previous work on the monitoring of largely non-reactive gases, such as carbon dioxide, has been based on infra-red (IR) optical absorption methods carried out at certain infra-red wavelengths. Such techniques require costly optical components which transmit at these long wavelengths, and which do not assist in miniaturization of the equipment in a manner applicable to the provision of a roadside diagnostic tool or other compact and portable instrument.

The legislative background in Europe and elsewhere to developments in this field is one in which legal requirements and administrative restrictions on exhaust emissions and other pollutants are becoming ever stricter, leading to a need for an item of test equipment which is compact and portable and readily used. Clearly, existing infra-red equipment does not meet this requirement.

Other background art in this field includes the following references:

1. J. Jackson, "Infra-red Gas Analyzers using Solid State Devices", Proc 1st Eur. Electro-optics Markets and Technology Conf. (IPC Sc. & Tech. Press, 1972, pp. 17–22.

2. J. D. Ingle & S. R. Crouch, "Spectrochemical Analysis", (Prentice-Hall Int. Ed., 1988), Chap. 3, sections 3 & 4, Chap. 4, section 6.

3. C. N. Banwell, "Fundamentals of Molecular Spectroscopy", Ed. 3 (McGraw-Hill, 1983), Chap. 3 section 8.

4. A. Mills & H. N. Murray, "Carbon Dioxide Monitor", International Patent Application WO91/05252, 1991.

5. A. Mills & H. N. Murray, U.S. patent application Ser. No. 07/853753, 1992.

6. H. N. McMurray, "Novel thin optical film sensors for the detection of carbon dioxide", J Mat. Chem., 2(4), 401–406, 1992.

7. A. Mills, Quing Chang & H. N. Murray, "Equilibrium studies on calorimetric plastic film sensors for carbon dioxide", Anal. Chem. 64, 1383–1389, 1992.

8. J. Watson, R. Tamadoni-Jahromi, N. McMurray & G. S. V. Coles, "A Gas Monitoring Instrument Comprising Fibre Optic, Piezoelectric and Gas-Sensitive Polymer Devices", Transducers '95, Stockholm, June 1995.

There is disclosed in item 4 of the above list of references, namely WO91/05252, published on Apr. 18, 1991, a carbon dioxide monitor which provides a detectable indication of the presence of an elevated proportion of carbon dioxide compared to that in normal ambient air. A substrate is coated with a mixture of a transparent plasticized polymer vehicle carrying an indicator material which undergoes a color change on exposure to carbon dioxide. The device is used to provide an indication of correct intubation of the trachea of a patient.

There has also been proposed a system for analysis of gas or vapor samples in which a test sample and a reference sample in respective containers are alternately passed through an infra-red beam while carried on a rapidly rotating mounting. This technique permits an effective analytical procedure but imposes serious size and cost and maneuverability penalties due to the technique for sequential alternate treatment of the test and reference samples with the infra-red beam.

Reference is also directed to U.S. patents:
U.S. Pat. No. 3,667,293
U.S. Pat. No. 4,467,236
U.S. Pat. No. 4,718,765
U.S. Pat. No. 4,914,719
U.S. Pat. No. 4,928,687
U.S. Pat. No. 4,994,117
U.S. Pat. No. 5,060,505
U.S. Pat. No. 5,071,526
U.S. Pat. No. 5,114,859
U.S. Pat. No. 5,184,017
U.S. Pat. No. 5,216,315
U.S. Pat. No. 5,252,828
U.S. Pat. No. 5,343,043
U.S. Pat. No. 5,375,592
U.S. Pat. No. 5,472,668

There is disclosed in the above U.S. '017 reference a gas analyzer for measuring concentrations of carbon dioxide in a vehicle exhaust which includes a sample gas chamber, a radiation emitter and a detector for determining radiation absorbed. A plurality of filters rotate through the radiation path to produce a time-multiplexed signal having concentration information for carbon dioxide and other gases. There is no disclosure in this reference, or in the other references of a method for electrometric analysis of a material sample, such as an automotive vehicle exhaust, comprising diverting incident radiation alternately in sequence onto two samples, one of which comprises the material to be analyzed, the sample comprising a reagent adapted to produce a calorimetric reaction with the material to be analyzed in the presence of said radiation, as disclosed in the embodiments described below.

SUMMARY OF THE INVENTION

An object of the invention is to provide a technique for monitoring carbon dioxide and/or other gases, and/or which technique may be reducible to practice in the form of compact and/or easily maneuverable equipment and/or suitable for use as a roadside automotive diagnostic aid, and/or which offers one or more other technical advantages identified herein.

According to the invention there is provided a method and apparatus for electrometric analysis as defined in the accompanying claims.

In an embodiment of the invention described below, there is provided a method and apparatus for electrometric analysis in which test and reference samples are alternately treated in sequence with light energy, and the result analyzed. In the embodiment, the light energy from a source passes alternately through the samples by means of a driven element interacting with the flow of radiation. The driven element is in the form of a radiation diverting element adapted to co-operate alternately and in sequence with at least two corresponding radiation receptors, each of these being arranged to feed radiation received to its respective one of the samples. In the embodiment the radiation diverting element is driven so as to effect the diversion of the radiation alternately in sequence through the samples. By such an arrangement the advantage is provided of an extremely simple and compact multiplexing arrangement, whereby the use of a piezo-electric bimorph as the drive means, or a corresponding equivalent drive, allows the apparatus to be constructed in the simple and compact form which roadside or similar usage requires.

Also in the embodiments described below there is provided the feature that the sample of material to be analyzed comprises a reagent adapted to produce a calorimetric reaction with the material to be analyzed, such as carbon dioxide. In this way the analysis of a material such as carbon dioxide is provided on a quantitative basis merely using a photometric technique. As a result, the quantitative analysis of such materials is transformed from a technique requiring infra-red spectroscopy and its attendant cost and complications and inherent lack of maneuverability, to a technique which has the potential to be constructed in extremely compact and easily used form.

In the described embodiment, the light energy source may be a controlled filament lamp, a light-emitting-diode or a solid-state laser, depending upon the absorption wavelengths of interest. This light, for example in the orange/red region of the spectrum, is injected into one end of an optical fibre, the other end of which is attached to the free end of a piezoelectric bimorph cantilever in such a way that the emergent light is collected sequentially by the ends of two further optical fibers, as shown in the drawings.

The output ends of these two fibers project their light components alternately through a sample cell and a reference cell and hence to a single sensor or photo-receptor in the form of a photodiode. The output from this receptor is fed to a microprocessor-based electronic circuit which determines the ratio of the intensity of the light passing through the sample cell to that passing through the reference cell. This ratio is likewise a measure of the ratio of optical absorption in the sample cell to that in the reference cell, and thus has the advantage of being independent of changes in the photo-receptor due to aging etc.

The sample and reference cells form two parts of a transparent cuvette into which can be inserted a glass slide coated with the gas-sensitive polymer which undergoes a color change, for example from blue to orange, when exposed to $CO_2$, and does so in a consistent and reversible manner. Hence, the amount of light allowed to cross the sample cell is a function of the $CO_2$ concentration, while the unaffected polymer in the reference cell provides a datum level.

Certain features of the invention are attained by providing a method for electrometric analysis of a material, comprising the steps of: (a) providing a flow of electromagnetic radiation from a source thereof, and (b) diverting the flow so as to feed the radiation alternately in sequence to two samples, one of which includes the material to be analyzed.

Other features of the invention are attained by providing apparatus for electrometric analysis of a test sample of a material to be analyzed, comprising: (a) a reference sample, (b) electromagnetic radiation receptors arranged to respectively feed received radiation to the test sample and the reference sample, (c) a source of a flow of electromagnetic radiation, and (d) diverting apparatus interacting with the flow of radiation and operable for diverting the flow of radiation for directing the flow alternately in sequence to said radiation receptors, thereby to alternately treat the samples with electromagnetic radiation from the source.

Still other features of the invention are attained by providing a method for analysis of a test sample of a material to be analyzed by reference to a corresponding reference sample, the method comprising the steps of: (a) reacting the material to be analyzed with a reagent in the test sample to produce a calorimetric change, and (b) analyzing the colorimetrically changed test sample by comparing it with the reference sample.

BRIEF DESCRIPTION OF THE DRAWINGS

Embodiments of the invention will now be described by way of example with reference to the accompanying drawings in which.

DESCRIPTION OF THE PREFERRED EMBODIMENT

Figure 1:
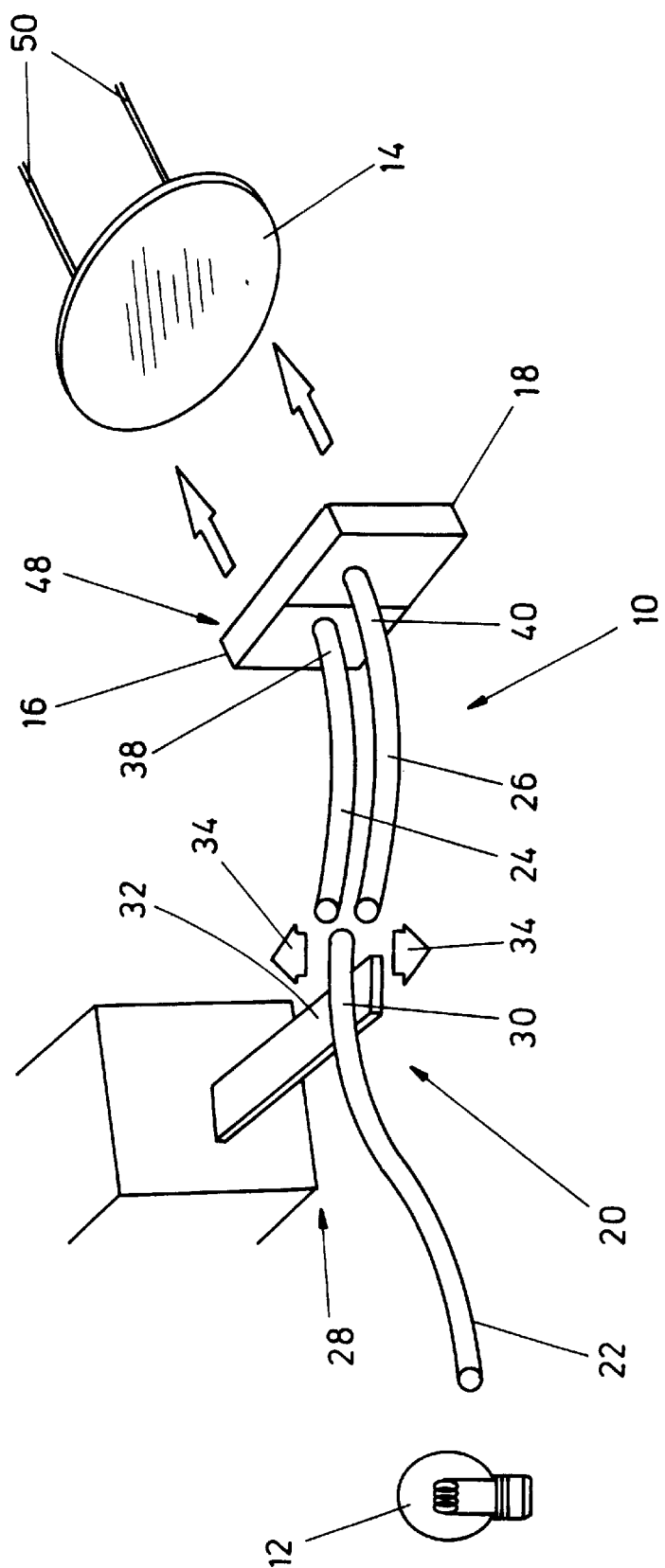
FIG. 1 shows a diagrammatic perspective view of the method and apparatus of the invention illustrating the relationship of the light source with the bimorph and the optical fibers, the samples and the photo-receptor.

As shown in FIG. 1, apparatus 10 for the photometric analysis of carbon dioxide comprises a light source 12, and a photoreceptor 14 in the form of a photo-diode to provide an output signal. A test cell 16 and a reference cell 18 are provided between light source 12 and photoreceptor 14 for test purposes, and a fibre-optic light path 20 is provided, between light source 12 and the cells 16, 18.

Light path 20 comprises primary and secondary optical fibers 22 and 24, 26 respectively. Associated with primary optical fibre 22 is a drive 28 associated with a radiation diverting element 30 constituted by the output end portion of primary optical fibre 22. This portion of the optical fibre is vibrated by drive 28 by the action of an output drive element 32 thereof. The direction of vibration is indicated in FIG. 1 by arrows 34, 36.

Not shown in FIG. 1 is associated apparatus adapting the analytical apparatus of FIG. 1 for use as a battery-driven roadside diagnostic system in which there is provided additionally a probe line or duct, a filter and a pump to generate an inflow of filtered gases to be monitored, these being delivered to test cell 16 for application to the sensory material therein, to be described more fully below.

Light source 12 is a controlled filament lamp. In alternative embodiments, a light-emitting diode or a solid-state laser may be substituted as the light source, depending upon the absorption wavelengths of interest.

Optical fibers 22, 24 and 26 are in inexpensive plastic form. One end of fibre 22 is located adjacent light source 12 and the other end is attached to the free end of drive element 32 of drive 28, which is in the form of a piezo-electric bimorph device.

Radiation diverting element 30 co-operates with receptor elements formed by the adjacent ends of optical fibers 24, 26 so as to feed radiation alternately from the primary fibre 22 to the secondary fibers 24 and 26 in turn as the primary fibre vibrates.

The output ends 38 and 40 of fibers 24 and 26 co-operate with the test and reference cells 16 and 18, respectively, so as to project their light energy alternately through the sample and reference cells and onwards to receptor 14, which is in the form of a silicon photo-diode.

Drive 28 is in the form of a piezoelectric bimorph and consists essentially of two flat plates of lead zirconite titanate (PZT) bonded together at their faces and given a polarity so that when an electric field is applied to the conductive layers covering their remaining faces, one plate lengthens while the other shortens, thus producing a bending action. The bimorph is mounted as a cantilever so that the free end of drive element 32 is able to vibrate under the influence of an applied alternating voltage. Radiation diverting element 30 is fixed to the free end of drive element 32 and the frequency of the electric supply to the drive is at the resistant frequency of the sub-system so as to produce maximum amplitude, for example a frequency of 120 hertz.

Figure 2:
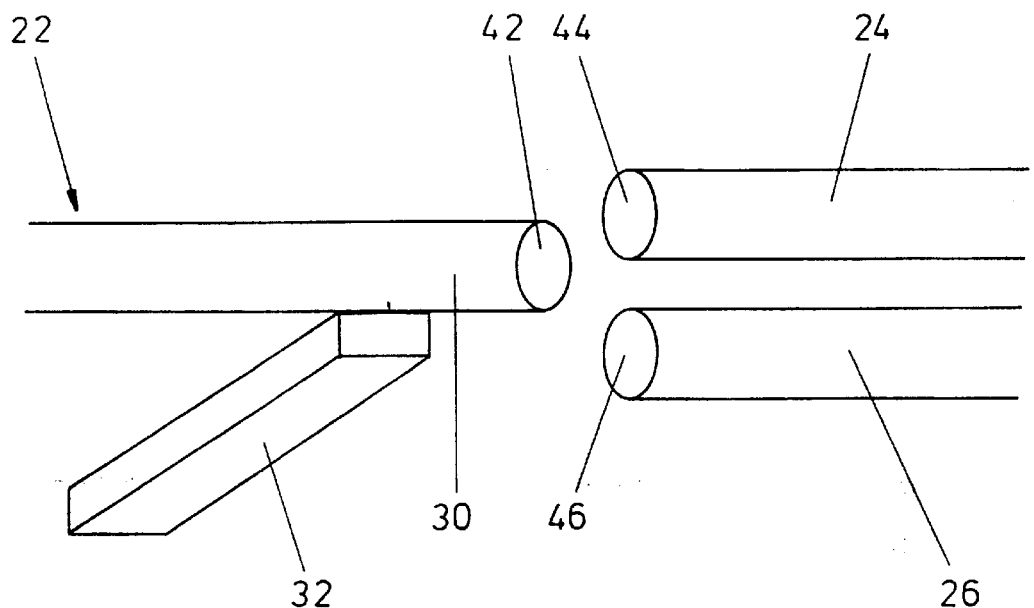
FIG. 2 shows a diagrammatic representation of the relationship between the single fibre-optic diverting element and the twin fibre-optic receptor elements.

FIG. 2 shows on a larger scale the positional relationship between the fibre-optic elements 22, 24 and 26, and the location of drive element 32 for effecting lateral movement of the radiation diverting element portion 30 of element 22 for the purposes at hand.

To minimize energy losses in transmission of light between the relevant ends 42, 44 and 46 of the fibre optic element seen in FIG. 2, the following principles apply, namely maximizing end-area overlap (as viewed lengthwise of the fibre-optic elements as seen in FIG. 2), and minimizing the length of the air transmission path between the adjacent ends. With the first of these factors in mind, the light-receiving ends 44 and 46 of elements 24 and 26 may be constructed so as to be larger than the light-transmitting end 42 of element 22. It is noted that the geometrical relationship between the light-transmitting and light receiving ends does affect the shape of the electrical waveform produced by the photo-diode 14.

Turning now to the construction of the cells 16 and 18, in this embodiment these test and reference cells are constructed as two parts of a transparent cuvette into which can be inserted a glass slide coated with the colorimetric reagent which produces a calorimetric reaction with the carbon dioxide to be analyzed. The reagent is a gas-sensitive polymer which undergoes a color change from blue to orange when exposed to carbon dioxide, and does so in a consistent and reversible manner. In this embodiment, the reagent is a quaternary alkyl-ammonium salt of an acid-base indicator dye. In this connection, reference is hereby directed to published specification W091/05252, the entire technical disclosure of which is hereby incorporated into the present application for disclosure purposes. It is noted that on page 3 of this published specification there is a reference to the possibility of obtaining a quantitative indication of carbon dioxide concentration by use of a spectrophotometric technique, but there is no disclosure relating to the measurement of $CO_2$ concentration using a technique based upon a non-spectroscopic approach which could be adapted to use in a compact form outside the laboratory.

The gas-sensitive reagent comprises a plasticized polymer in which are dissolved organo-soluble quaternary alkyl-ammonium salts of acid-base indicator dyes. This reagent is dissolved in a volatile organic solvent and cast from solution to form a thin (10 to 100 micro-meters) transparent films. These films have the characteristic that their optical density or absorbance, or fluorescent intensity, is strongly influenced by the concentration of carbon dioxide. The films are completely insoluble in water and contain no residual volatile components and thus function over wide ranges of temperature and relative humidity. The reaction with carbon dioxide has been explained in terms of a protonic equilibrium involving the quaternary alkyl-ammonium salts of the indicator acids, water molecules associated with the salts, and carbonic acid. These materials make it possible to prepare sensors which combine the properties of rapid (sub-section) response with long-term chemical and physical stability (storage lives exceeding a year) and the ability to survive biological sterilization by gamma radiation.

The specific carbon dioxide-sensitive reagent used in this embodiment is an example of a general class of thin optical film sensors suitable for use with a wide range of gases, both acidic and alkaline. It is noted that films incorporating organo-soluble salts of the ruthenium (II) tris-bipyridyl cation have been shown to act as reversible non-consumptive oxygen sensors operating via a lumiscence-quenching mechanism, and thus offer the possibility of a corresponding facility for quantitative oxygen monitoring.

Although not shown in FIG. 1, the cuvette 48 is constructed so that test cell 16 is open to the gas flow to be sampled while reference cell 18 is gas tight and sealed from this flow, and is filled with clean air. For test purposes, a tubular probe and associated gas flow-producing fan is provided to induce the necessary rate of gas flow across the test cell 16 from the gas source to be sampled.

In use, the quantum or amount of light from source 12 passing through test cell 16, as permitted by the calorimetric reaction of the reagent therein, is a function of the $CO_2$ gas concentration in the gas flow at the relevant time. The unaffected reagent in reference cell 18 provides a datum level.

Cuvette 48 is constructed to permit quick and easy insertion and removal of glass slides coated with the gas-sensitive polymetric reagent.

The photo diode 14 produces a corresponding emf at output connections 50 which provides a means for analyzing the $CO_2$ gas content applied to test cell 16. This is achieved by means of the electronic circuit illustrated in FIG. 3.

Figure 3:
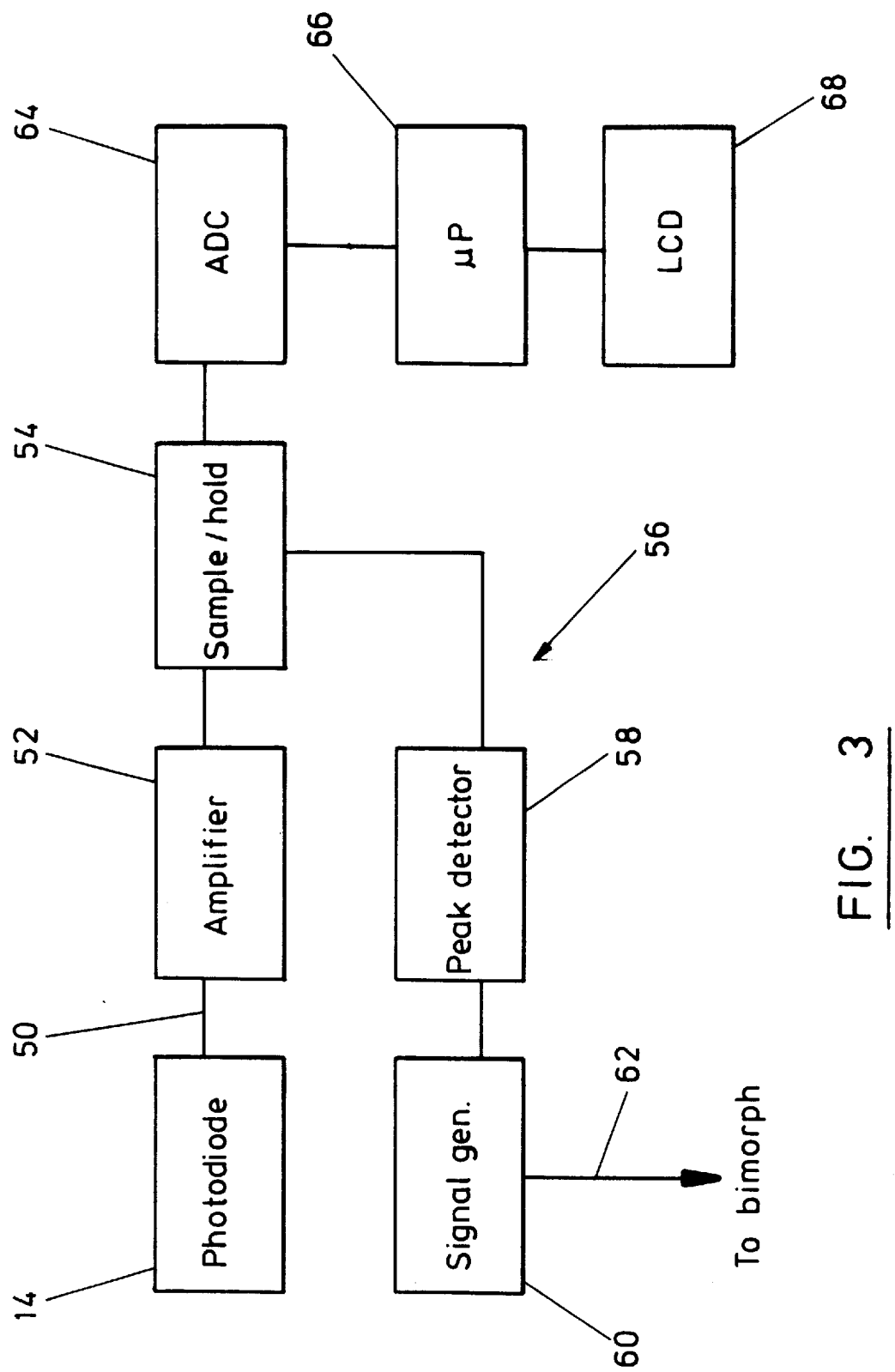
FIG. 3 shows in block diagram form the electronic system of the apparatus.

As shown in FIG. 3, the signal from photo diode 14 is passed to an amplifier 52, and then to a signal sample-and-hold circuit 54, which is synchronized with the oscillation of bimorph 28, and effectively generates a square wave representing the peak values of the signals produced by photo diode 14 from the test and reference cells.

A feed-back loop 56 to bimorph drive 28 comprises a peak detector 58 and a signal generator 60 having an output indicated at 62 to be fed to the bimorph 28, to provide the required synchronization function.

The output from sample/hold circuit 54 is applied to an analogue-to-digital convertor (ADC) 64 and then to a microprocessor 66 producing a final readout on a liquid crystal display 68 in terms of relative optical density of the two cells, and indeed in terms of percentage carbon dioxide, after calibration, as discussed below.

The interpretation and calibration of the apparatus will now be described with reference to FIGS. 4 and 5.

Figure 4:
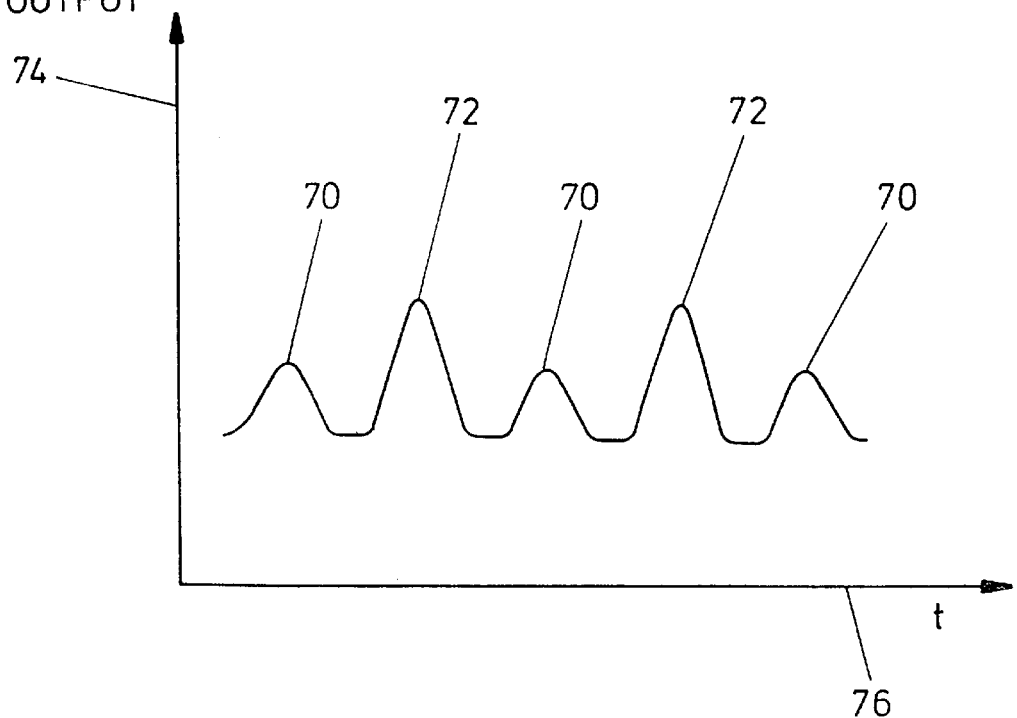
FIG. 4 shows a sample output waveform from the photo-diode forming the receptor in the apparatus of FIG. 1.

FIG. 4 shows the output from photo-diode 14. The differing amplitudes of peaks 70, 72, in the plot of photo diode output 74 against time 76, correspond to the test and reference cell absorbencies.

The amplitude of the waveform between successive peaks is not zero because, at the mid point of the travel of radiation diverting element 30, light enters both of the fibre-optic elements 24 and 26. A sampling technique is used to determine the true effective amplitudes of the signals corresponding to peaks 70 and 72.

For calibration purposes, the test cell 16 is replaced by a sequence of neutral density filters, and the ratio of the peak amplitudes of the corresponding series of sample signals to that of the reference signal is converted to optical density form.

Figure 5:
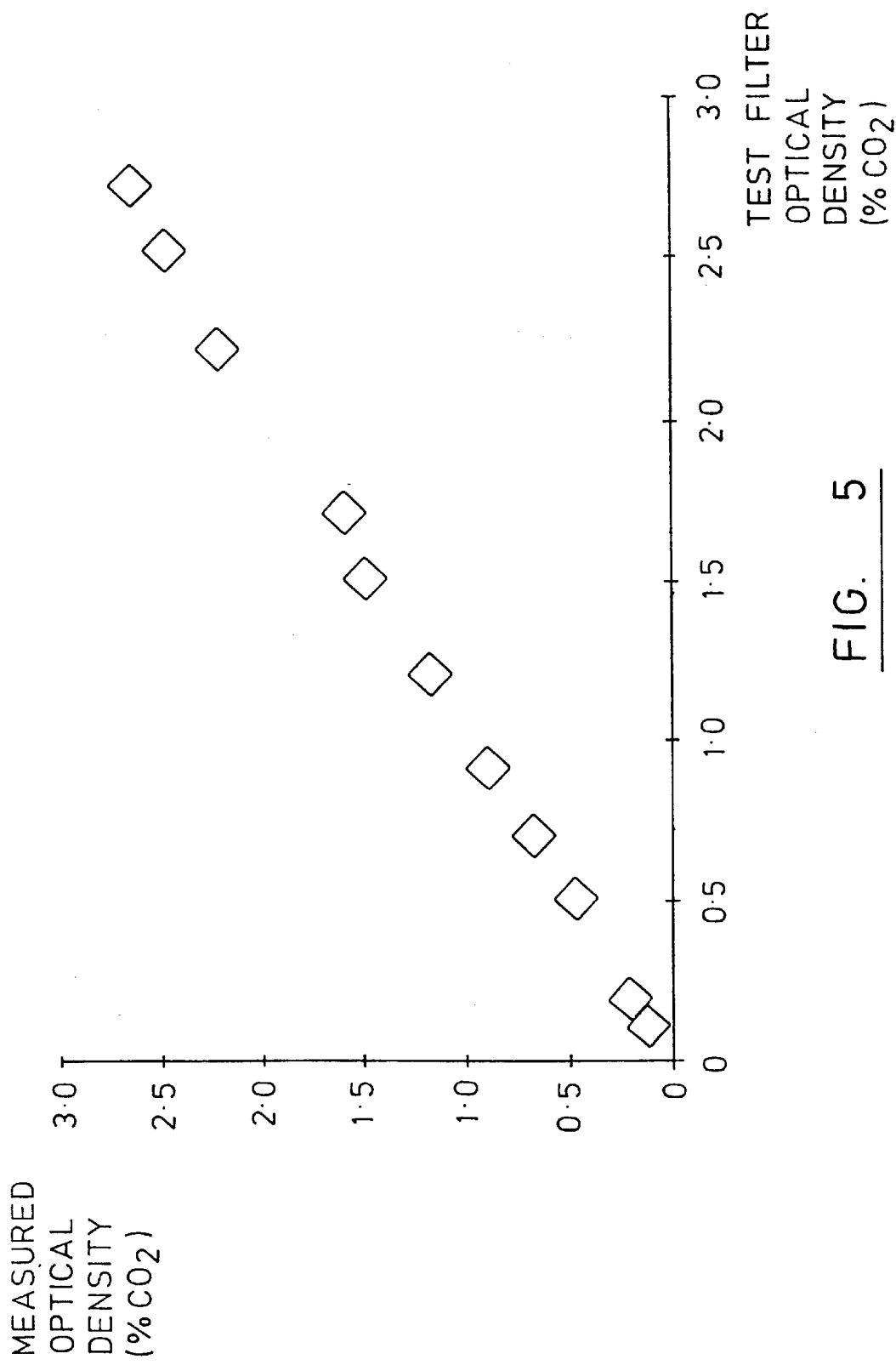
FIG. 5 shows a plot of the output optical density of the test cell plotted against the corresponding density of the reference cell.

FIG. 5 shows the result of test work in which measured optical density is plotted against actual optical density and thus the correspondence between the plotted values on the two scales provides an indication of the accuracy and consistency of the technique. As FIG. 5 shows, the correspondence between the values on the two scales is indicative of close correlation, whereby calibration of optical density in units of percentage concentration carbon dioxide is clearly a matter of simple interpretation.

Amongst other modifications which could be made in the above-described embodiments while remaining within the scope of the invention as presently envisaged are the following:

1. The use of alternative energy sources instead of light source 12, although it is expected that the use of visible light energy will be the most convenient source;

2. Modification of the technique for splitting the light energy between the test and reference cell samples, although it is expected that the use of a driven or vibrated energy diverting element which moves in a back-and-forth manner will be a consistent feature of practical embodiments. It might be possible to provide for the driven end of the moveable fibre optic element to move in a short radius circular path with the circular path center located centrally between the fixed receptor fibre-optic elements;

3. Minimization of energy losses at the interface between the fibre-optic elements by use of optically polished sliding block end faces on the diverter and receptor elements;

4. The photoreceptor or energy-converting device 14 may be of any convenient form capable of providing an appropriate output signal from the incident energy source utilized; and 5. Considerable variation in the structure and arrangement of the test and reference cells and the slide insertable therein is envisaged in order to provide for convenience of use and reliability of operation in a mobile diagnostic instrument.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A compact, portable electrometric apparatus for roadside analysis of exhaust emissions of automotive vehicles, comprising:

a test cell containing a test sample of exhaust emissions to be analyzed, said test cell including a reagent reactive with the test sample upon exposure thereto for producing a calorimetric change, a reference cell containing a reference sample, two fiber optic light guides each having an input disposed to receive electromagnetic radiation and an output, said outputs being disposed for respectively directing electromagnetic radiation to the test cell and the reference cell, an electromagnetic radiation flow source, and diverting mechanism including a piezoelectric bimorph coupled to the electromagnetic radiation flow source for diversion thereof to direct the electromagnetic radiation flow alternately in sequence to the inputs of said light guides.

2. The apparatus of claim 1, wherein said diverting mechanism includes a fiber optic element for directing the flow of electromagnetic radiation.

3. The apparatus of claim 1, and further comprising a sensor disposed for sensing electromagnetic radiation emitted from said test cell and said reference cell in response to the direction of electromagnetic radiation thereto.

4. The apparatus of claim 3, wherein said sensor is disposed on the side of said test cell and said reference cell opposite said light guides for receiving electromagnetic radiation after it has passed through the samples and the reagent.

* * * * *